United States Patent
Forsgren-Brusk et al.

(10) Patent No.: US 6,649,806 B1
(45) Date of Patent: Nov. 18, 2003

(54) ABSORBENT ARTICLES

(75) Inventors: Ulla Forsgren-Brusk, Pixbo (SE); Bo Runeman, Jonsered (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/856,562

(22) PCT Filed: Dec. 15, 1999

(86) PCT No.: PCT/SE99/02369

§ 371 (c)(1),
(2), (4) Date: May 23, 2001

(87) PCT Pub. No.: WO00/35502

PCT Pub. Date: Jun. 22, 2000

(30) Foreign Application Priority Data

Dec. 16, 1998 (SE) ................................................ 9804390

(51) Int. Cl.[7] ................................................ A61F 13/15
(52) U.S. Cl. ........................................ 604/360; 604/368
(58) Field of Search ................................ 604/359, 360, 604/368

(56) References Cited

U.S. PATENT DOCUMENTS

| | | | |
|---|---|---|---|
| 3,794,034 A | | 2/1974 | Jones, Sr. |
| 4,685,909 A | * | 8/1987 | Berg et al. ............ 604/360 |
| 5,698,688 A | * | 12/1997 | Smith et al. ............ 536/56 |
| 5,817,362 A | * | 10/1998 | Vandenbergh et al. ...... 424/115 |
| 6,020,453 A | * | 2/2000 | Larsson et al. ............ 428/480 |
| 6,187,990 B1 | * | 2/2001 | Runeman et al. .......... 604/360 |
| 2003/0012810 A1 | * | 1/2003 | Cintio et al. ................ 424/443 |

FOREIGN PATENT DOCUMENTS

| | | | |
|---|---|---|---|
| EP | 0 311 344 | | 4/1989 |
| WO | WO 92/13577 | * | 8/1992 ........... A61L/15/36 |
| WO | 97/02846 | | 1/1997 |
| WO | WO 98/44884 | * | 10/1998 ........... A61F/13/20 |

* cited by examiner

Primary Examiner—Weilun Lo
Assistant Examiner—C. Lynne Anderson
(74) Attorney, Agent, or Firm—Burns, Doane, Swecker & Mathis, L.L.P.

(57) ABSTRACT

The invention relates to an absorbent article that includes a synergistic combination of a) a pH-regulating substance in the form of a partially neutralized superabsorbent material, and b) lactic acid bacteria wherein after being wetted and worn close to the skin, the article has a pH value in the range of 3.5–5.5, preferably within the range of 3.5–4.9, and most preferably within the range of 4.1–4.7.

12 Claims, 2 Drawing Sheets

Cultivation of E-coli

Cultivation of E-coli

Cultivation of Ent. Faecalis

ABSORBENT ARTICLES

FIELD OF INVENTION

Figure 1:
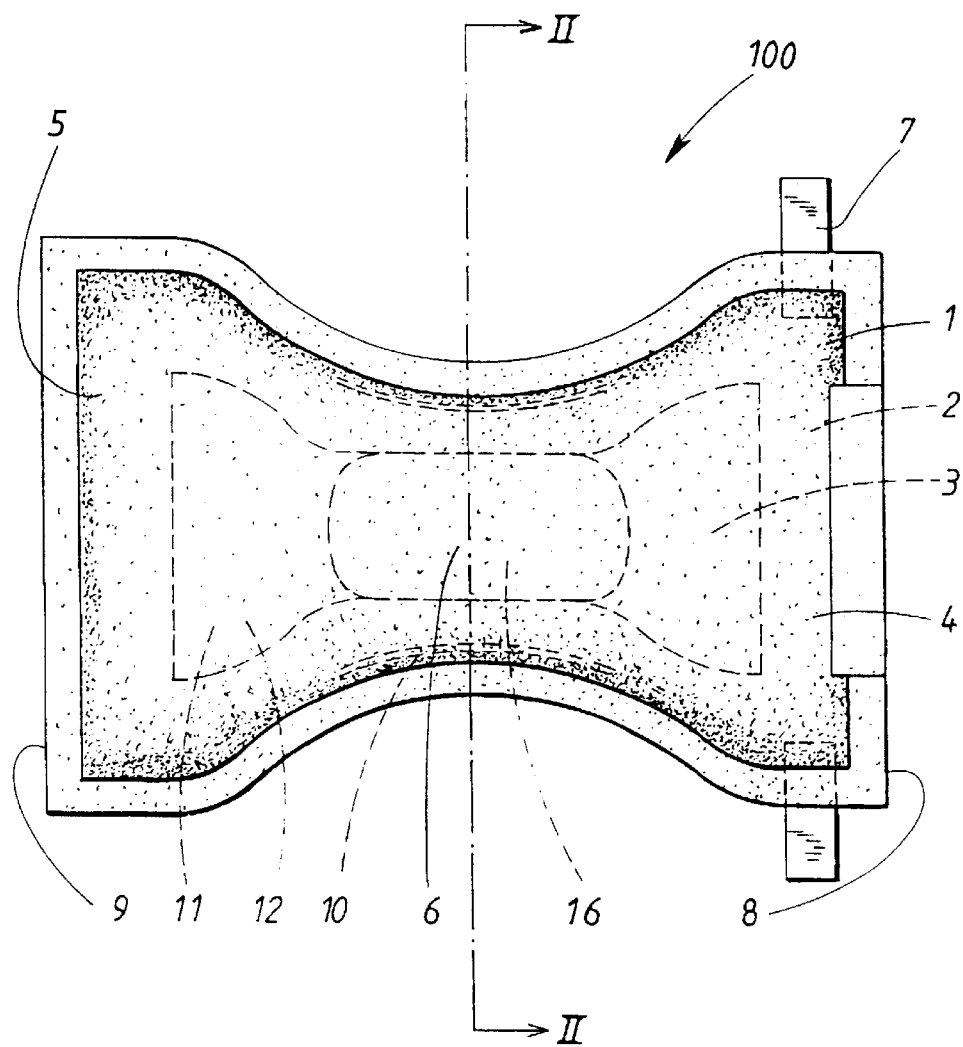

The present invention relates to absorbent articles of the kind that are worn in contact with the wearer's skin, such as diapers, incontinence protectors, sanitary napkins and like articles. The invention also relates to methods of reducing the undesired side effects that may sometimes occur when using such articles.

KNOWN TECHNIQUES

Absorbent articles of this kind are known in many different forms. The absorbent body of such products is conventionally produced by dry-defibring cellulose pulp, e.g. cellulose pulp in roll, bale or sheet form, and converting the dry-defibred pulp in a fluffed state to a pulp mat, sometimes with an admixture of so-called superabsorbents. Superabsorbents are polymers that are able to absorb several times their own weight of water or body fluid.

A typical problem relating to absorbent articles such as diapers, sanitary napkins, incontinence protectors or the like is that their use can lead to undesired side effects, such as skin irritation and malodours. These problems can occur as a result of occlusion, the presence of moisture, and factors of a mechanical, microbial and enzymatic nature, all of which coact with and amplify the effect of one another to different extents. For instance, several undesired side effects can occur as a result of or in conjunction with an increase in pH.

U.S. Pat. No. 3,794,034 describes the significance of pH in an absorbent article and also teaches impregnation of the article with buffering substances by means of which the pH in the article can be kept between 3.5–6.0, which is beneficial both with respect to the inhibition of the growth of undesired bacteria and therewith the occurrence of undesirable odours, and also in avoiding negative skin affects.

EP 0.311,344 describes controlling pH in absorbent articles, wherein the buffering properties are obtained with the aid of a partially neutralised superabsorbent material and an antimicrobial substance chosen from among ordinary nitrogen-based compounds or bis-guanide compounds. The undesirable side effects can be reduced, by controlling the pH of the article so that it will not exceed a given level. However, not all harmful microorganisms are influenced negatively by a low pH value. *Escherichia coli*, which is itself acid-producing, is an example of such a microorganism. The antimicrobial substances can also give rise to problems. For instance, these substances can give rise to allergies or skin irritation with long-time use. Moreover, general discussions are ongoing as to whether or not comprehensive use of antibiotics can result in an increasing resistance of harmful bacteria strains to antibiotics. Finally, the use of antibiotics can have negative ecological consequences with regard to the handling of waste.

Attempts to solve the aforesaid problems of undesirable odours and the growth of undesirable microorganisms have also been made by actively adding specific mricroorganisms to absorbent articles of the aforesaid kind. For example, one such technique is described in WO 97/02846. These specific microorganisms are primarily lactic acid producing bacteria, such as different species of the strains Lactobacillus and Lactococcus, which have an antagonistic effect on other microorganisms.

However, the aforedescribed known techniques have not completely eliminated the problems of undesirable odours and the growth of undesirable microorganisms. Consequently, there is a need for improvements that can further reduce the problems associated with malodours and the growth of microorganisms.

SUMMARY OF THE INVENTION

It has now surprisingly been found that the aforesaid problems associated with undesirable side effects, such as malodours and skin irritation, can be reduced still further by using an absorbent article that contains a synergistic combination of a) a pH-regulating substance in the form of a partially neutralised superabsorbent material, and b) lactic acid bacteria, where the pH value of said article subsequent to being wetted when worn against the skin lies in the range of 3.5–5.5, preferably within the range of 3.5–4.9, and most preferably within the range of 4.1–4.7.

DEFINITIONS

The term "absorbent article" as used in this document relates to absorbent articles that are worn against the skin, such as diapers, incontinence protectors and sanitary napkins.

The term "superabsorbent" and the acronym "SAP" relates to polymers that are able to absorb several times their own weight of water or body fluid. A suitable partially neutralised superabsorbent material may be comprised of a cross-linked polyacrylate of the kind described in EP 0,392, 108, although other types of superabsorbent material that have corresponding properties may alternatively be used.

The term "lactic acid bacteria" and the abbreviation "LB" relate to a group of bacteria which produce lactic acid at normal fermentation. Examples of bacteria species that include strains belonging to this group are Lactobacillus, Lactococcus, Leuconostoc and Pediococcus. Bacteria of the families Lactobacillus and Lactococcus are preferred.

The term "CTMP" relates to chemithermomechanical pulp.

The Term "CP" relates to chemical cellulose pulp.

The term cfu relates to colony-forming units.

Figure 2:
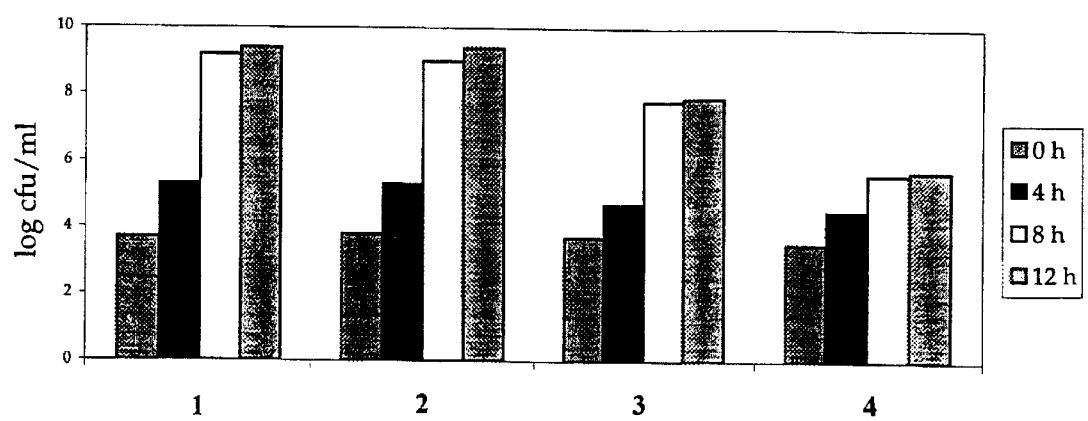
Figure 3:
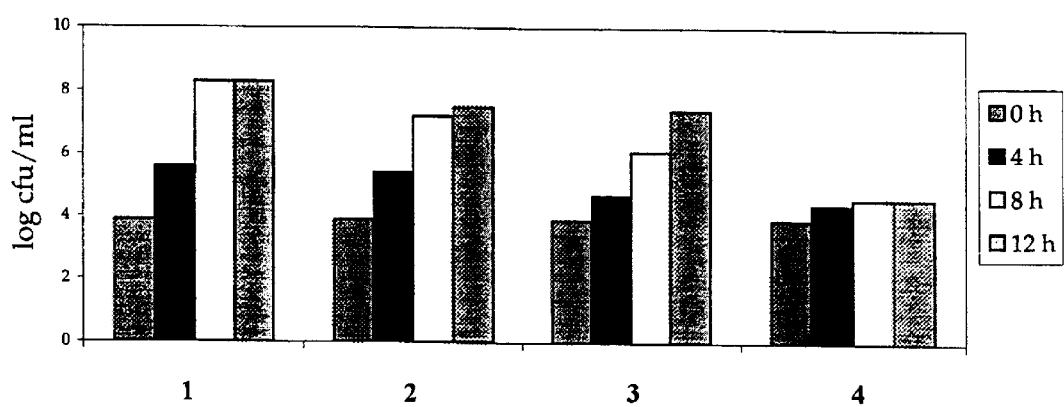

The invention will now be described with reference to the accompanying drawings, in which FIG. 1 shows an inventive diaper from that side which is intended to lie against the wearer in use;

FIG. 2 is a stack diagram illustrating the cultivatation of *Escherichia coli* in an absorbent article containing 1) CTMP+conventional superabsorbent; 2) CTMP+conventional superabsorbent+lactic acid bacteria; 3) CTMP+partially neutralised superabsorbent; and 4) CTMP+lactic acid bacteria+partially neutralised superabsorbent; and FIG. 3 is a stack diagram illustrating the cultivation of *Enterococcus faecalis* in an absorbent article that contains 1) CTMP+conventional superabsorbent; 2) CTMP+conventional superabsorbent+lactic acid bacteria; 3) CTMP+partially neutralised superabsorbent; and 4) CTMP+lactic acid bacteria+partially neutralised superabsorbent.

DETAILED DESCRIPTION OF THE INVENTION

An absorbent article with which the problem associated with undesirable side effects, such as skin irritation and undesirable odours, is further reduced by combining in said article a pH-regulating substance in the form of a partially neutralised superabsorbent material, with lactic acid bacteria.

Swedish Patent Application 9702298-2 describes an absorbent article that includes a pH-regulating substance in the form of a partially neutralised superabsorbent material which when wetted produces in the absorbent article a pH in the range of 3.5–4.9. Such a pH value has been found to have a growth-inhibiting effect on undesirable microorganisms in the article. The activity of certain skin-affecting enzymes, such as lipases and proteases, is also impaired.

According to the invention, an absorbent body may also include absorbent material other than partially neutralised superabsorbent material. Cellulose pulp is an example of one such material. It has been found beneficial to use a partially neutralised superabsorbent material according to the aforegoing in combination with cellulose that has a pH below 7, and preferably below 6. A suitable cellulose pulp is chemithermomechanical pulp (CTMP) having a pH=2.5–8.5, preferably 2.5–6.5, and most preferably 2.5–5.5. Another suitable pulp is chemical cellulose pulp that has a pH=2.5–8.5, preferably 2.5–8.0 and most preferably 2.5–7.0.

The cellulose pulp can be given a suitable acidity by controlling the pH of the pulp during the manufacturing process, for instance by adding an acidifier. This acidifier may, for instance, be $SO_2$-water. Alternatively, an appropriate acid may be added to the finished pulp.

As before mentioned, cross-linked superabsorbent polyacrylates suitable for use in the present invention are described in EP 0,391,108. Other superabsorbent materials having the same properties as those aforesaid may also be used. A suitable proportion of superabsorbent material in the article is 5–100%, preferably 15–60% and most preferably 15–50%.

SE 9702298-2 describes the relationship between the degree of neutralisation and the pH of the aforesaid superabsorbent material. It is evident that the degree of neutralisation will preferably be between 20% and 45%, and more preferably between 20% and 35%.

The diaper 100 shown in FIG. 1 includes a liquid-permeable casing sheet 1 made, for instance, of nonwoven material or of perforated plastic film, a liquid-impermeable casing sheet 2, made for instance of plastic film or hydrophobic nonwoven, and an absorbent body 3 enclosed between said casing sheets 1, 2.

The diaper is intended to embrace the lower part of the wearer's trunk in the form of a pair of absorbent underpants. Accordingly, the diaper includes two end pails 4, 5 and a narrower crotch part 6 between said end parts, said crotch part being intended to be placed between the thighs of the wearer in the crotch region when in use. The diaper includes fastener tabs 7 close to the rear waist edge 8 of the diaper, so as to enable the diaper to be secured in the desired pants-like configuration. In use, the fastener tabs 7 are fastened to the front part 5 of the diaper, close to the front waist edge 9, so as to hold the diaper together around the wearer's waist.

The diaper shown in FIG. 1 also includes prestretched elastic devices 10, which may consist of elastic tape, wire covered elastic treads, elastic foam or some other suitable material. For the sake of simplicity, the elastic devices 10 have been shown in a stretched state in FIG. 1. As soon as the tension in the elastic devices is released, the devices will contract and therewith form elastic leg openings on the diaper.

The absorbent body 3 of the diaper embodiment shown in FIG. 1 is comprised of two layers 11, 12, to wit an upper liquid acquisition layer 11 and a lower liquid storing and liquid dispersing layer 12. The upper acquisition layer 11 shall be capable of receiving large volumes of liquid over a short period of time, i.e. shall have a high instantaneous liquid absorption capacity, whereas the lower liquid storing and dispersing layer 12 shall have a high liquid dispersion capacity and shall be able to drain liquid from the acquisition layer 11 and disperse this liquid in the storage and dispersion layer 12. The differences in the respective properties of the two layers 11 and 12 can be achieved by arranging for differences in density, wherewith a more densely compressed fibre structure will disperse liquid more effectively than a corresponding fibre structure of lower density, which as a result of its larger pore size has a higher instantaneous liquid absorption capacity and a lower liquid dispersion capacity. Differences in the absorption capacity of the two layers can also be achieved with the aid of different fibre structures that have mutually different properties. For instance, chemically produced cellulose fluff pulp has a higher liquid dispersion capacity than, e.g., pulp that is produced mechanically or chemithermomechanically, so-called CTMP. A fibre structure that contains chemically stiffened cellulose fibres still also have a higher liquid absorption capacity but lower liquid dispersion capacity than conventional chemical pulp. Natural fibre wadding or fluffy nonwoven material are examples of other materials suitable for use in the acquisition layer 11.

A pH-lowering substance in the form of a partially neutralised superabsorbent is mixed in with the upper liquid acquisition layer 11 of the absorbent body 3. This part of the absorbent body 3 also includes lactic acid bacteria.

A partially neutralised superabsorbent that functions as a pH-regulating substance has a lower total absorption capacity and a slower absorption rate than conventional superabsorbent. One advantage with placing such a superabsorbent in the upper part of the absorbent body closest to the wearer is that the risk of swollen superabsorbent lumping together is reduced in this way. A common problem is so-called gel blocking caused by clumping of swollen superabsorbent. Gel blocking implies that when the superabsorbent is wetted it forms a gel that blocks the pores in the porous structure and therewith impedes the transportation of liquid from the wetting region to other parts of the absorbent structure.

A conventional superabsorbent is mixed in the lower liquid storage and liquid dispersion layer 12 of the absorbent body 3. One advantage afforded by placing conventional superabsorbent in the lower liquid storage layer 12 is that a conventional superabsorbent has a higher total absorption capacity than a partially neutralised superabsorbent that has a pH-regulating effect.

It will be understood that the invention also includes other absorbent body constructions. The absorbent body may include both partially neutralised superabsorbent and conventional superabsorbent, both of said superabsorbents being distributed uniformly in both the upper layer and the lower layer of the absorbent body. Furthermore, it is feasible to use only one type of superabsorbent material in addition to cellulose fluff pulp. In such cases, the superabsorbent material has the form of a superabsorbent which will also function as a pH-regulating substance.

Layers other than the liquid acquisition layer 11 in the absorbent body 3 may also include lactic acid bacteria, and it is also feasible to include lactic acid bacteria on/in the liquid permeable casing sheet of said article.

The invention will now be described with reference to the following example, which is given for illustration purposes only and which has no limiting effect on the invention.

EXAMPLE

Tests were carried out while using sterile synthetic urine that included a microorganism growth medium. The synthetic urine contained monoions, divalent ions, cations and anions and the urine was prepared in accordance with information contained in Geigy, Scientific Tables, Vol. 2, 8th Ed., 1981, page 53. The microorganism growth medium was based on information concerning Hook and FSA media for enterobacteria. The mixture had a pH of 6.6.

Absorbent bodies were produced with the aid of a slightly modified sample body former according to SCAN C 33:80. Fluff pulp and superabsorbent material of a desired type were weighed-up and a uniform mixture of fluff pulp and superabsorbent material then passed in an air stream at a subpressure of about 85 mbar through a tube having a diameter of 5 cm and provided with a metal bottom net on which thin tissue had been placed. The mixture of fluff pulp and superabsorbent material was collected on the tissue on the metal net and formed the absorbent body. The absorbent body was then weighed and compressed to a bulk density of 6–12 cm$^3$/g. The absorbent bodies contained 0.85 g CTMP and 0.15 g superabsorbent material. Two different superabsorbents were used, these being conventional superabsorbent having a pH of about 6 and partially neutralised superabsorbent having a pH of about 4.2. In the event of using lactic acid bacteria, these bacteria comprised *Lactobacillus plantarum*, strain LB931, which had been deposited at Deutsche Sammlung von Mikroorganismen (Braunschweig, Del.) and given the deposition number DSM 11918. LB931 was freeze-dried in skimmed milk. The bacteria concentration was adjusted to $10^9$–$10^{10}$ cfu/gram, by mixing the bacteria with powdered skimmed milk.

Absorbent bodies were prepared in accordance with the above method. Synthetic urine was prepared in accordance with the aforegoing. *Escherichia coli* (*E.c.*) and *Enterococcus faecalis* (*E.f.*) were cultivated in nutrient broth (Nutrient Broth Oxoid CM1) overnight at a temperature of 30° C. The graft cultures were diluted and the bacteria contents calculated. The cultures were mixed in different proportions, so that the final culture mix contained about $10^4$ organisms per ml of synthetic urine. 10 ml of the synthetic urine were poured into a sterile sputum jar 70.5×52 mm, volume 100 ml, and the absorbent body placed upside down in the jar and allowed to absorb liquid for a period of 5 minutes, whereafter the jar was turned and incubated at 35° C. for 0, 4, 8 and 12 hours respectively, whereafter the bacteria count in the absorbent body was determined. TGE agar was used in the cultivating process for measuring the total number of bacteria, and Drigalski agar and Slanetz Bartley agar were used for specific measurement of *Escherichia coli* and *Enterococcus faecalis* respectively. LB931 was calculated on MRS agar (de Man Rogosa Sharpe). When LB931 was added to the absorbent body, it was added in an amount corresponding to 10 mg of the freeze-dried mixture mixed with 10 ml synthetic urine, which was then added immediately to the sample body.

The results of these tests are listed in the following table:

Bacteria growth in absorbent articles with or without partially neutralised superabsorbents and lactic acid bacteria respectively.

| Type of absorption body | 0 h log cfu/ml | 4 h " | 8 h " | 12 h " |
|---|---|---|---|---|
| I. *E. Coli*: | | | | |
| CTMP + SAP | 3.7 | 5.3 | 9.2 | 9.4 |
| CTMP + SAP + LB | 3.8 | 5.3 | 9.0 | 9.4 |
| CTMP + acid SAP | 3.7 | 4.7 | 7.8 | 9.0 |
| CTMP + acid SAP + LB | 3.5 | 4.5 | 5.6 | 5.7 |
| II. *Enterococcus faecalis*: | | | | |
| CTMP + SAP | 3.9 | 5.6 | 8.3 | 8.3 |
| CTMP + SAP + LB | 3.9 | 5.4 | 7.2 | 7.5 |
| CTMP + acid SAP | 3.9 | 4.7 | 6.1 | 7.4 |
| CTMP + acid SAP + LB III. LB931: | 3.9 | 4.4 | 4.6 | 4.6 |
| CTMP + SAP + LB | 7.7 | 7.8 | 8.4 | 8.5 |
| CTMP + acid SAP + LB | 7.5 | 7.9 | 8.5 | 8.7 |

Partially neutralised superabsorbent is designated "acid SAP" in the above table.

It will be evident from the table that the combination of partially neutralised superabsorbent and lactic acid bacteria has a synergistic effect with regard to the reduction in the growth of *Escherichia coli* and *Enterococcus faecalis*. The division III in the above table also shows that LB931 grow equally as well in the presence of partially neutralised superabsorbent as in the presence of conventional superabsorbent.

These results are also shown in FIGS. 2 and 3.

What is claimed is:

1. An absorbent article that includes a synergistic combination of
   a) a pH-regulating substance in the form of a partially neutralized superabsorbent material, and
   b) lactic acid bacteria,
   where the pH value of said article after being wetted and when worn against the skin lies in the range of 3.5–5.5.

2. An absorbent article according to claim 1, wherein said article includes at least one further absorbent material.

3. An absorbent article according to claim 2, wherein the at least one further absorbent material includes chemithermomechanical cellulose pulp (CTMP).

4. An absorbent article according to claim 2, wherein the article includes chemical cellulose pulp (CP).

5. An absorbent article according to claim 1, wherein said lactic acid bacteria belong to the Lactobacillus family.

6. An absorbent article according to claim 5, wherein said lactic acid bacteria belong to the *Lacrobacillus plantarum* strain LB931, said strain having been deposited at Deutsche Sammlung von Microorganismen (Braunschweig, Del.) and there given the number DSM11918.

7. An absorbent article according to claim 3, wherein the pH of the cellulose pulp has been lowered by adding an acidifier during the pulp manufacturing process.

8. An absorbent article according to claim 2, wherein the article includes a casing-enclosed absorbent body which includes an upper liquid acquisition layer that includes partially neutralized superabsorbent material intended to lie proximal to the wearer in use, and a lower liquid storage and liquid dispersion layer which includes conventional superabsorbent material and which is intended to lie distal from the wearer in use.

9. An absorbent article according to claim 1, wherein the number of lactic acid bacteria in the article is $10^4$–$10^{11}$ cfu.

10. An absorbent article according to claim 9, wherein the number of lactic acid bacteria in the article is $10^6$–$10^{10}$ cfu.

11. The absorbent article of claim 1, wherein said pH value is in the range of 3.5–4.9.

12. The absorbent article of claim 11, wherein said pH value is in the range of 4.1–4.7.

* * * * *